(12) United States Patent
Haar et al.

(10) Patent No.: US 8,052,618 B2
(45) Date of Patent: Nov. 8, 2011

(54) DIAGNOSTIC TEST ELEMENT AND PROCESS FOR ITS PRODUCTION

(75) Inventors: Hans-Peter Haar, Wiesloch (DE); Karin Schwind, Schifferstadt (DE); Michael Marquant, Mannheim (DE); Nigel A. Surridge, Carmel, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/389,778

(22) Filed: Feb. 20, 2009

(65) Prior Publication Data

US 2009/0227898 A1    Sep. 10, 2009

Related U.S. Application Data

(63) Continuation of application No. PCT/US2007/065918, filed on Apr. 4, 2007.

(51) Int. Cl.
*A61B 5/151* (2006.01)

(52) U.S. Cl. ........................................ 600/583; 606/181

(58) Field of Classification Search .......... 606/181–183; 600/583
See application file for complete search history.

(56) References Cited

U.S. PATENT DOCUMENTS

| | | | | |
|---|---|---|---|---|
| 4,167,305 A | * | 9/1979 | Ichiba et al. | 385/141 |
| 4,211,591 A | * | 7/1980 | Stiles | 156/83 |
| 4,269,192 A | * | 5/1981 | Matsuo | 600/477 |
| 4,270,963 A | * | 6/1981 | Howat | 156/201 |
| 4,622,974 A | | 11/1986 | Coleman et al. | |
| 5,031,995 A | * | 7/1991 | Pinson | 385/102 |
| 5,195,162 A | * | 3/1993 | Sultan et al. | 385/130 |
| 5,282,950 A | * | 2/1994 | Dietze et al. | 204/406 |
| 5,607,401 A | * | 3/1997 | Humphrey | 604/239 |
| 6,032,059 A | | 2/2000 | Henning et al. | |
| 6,176,865 B1 | * | 1/2001 | Mauze et al. | 606/171 |
| 6,375,627 B1 | * | 4/2002 | Mauze et al. | 600/584 |
| 6,576,101 B1 | * | 6/2003 | Heller et al. | 204/403.14 |
| 6,584,335 B1 | * | 6/2003 | Haar et al. | 600/322 |
| 6,591,125 B1 | * | 7/2003 | Buse et al. | 600/347 |
| 6,830,551 B1 | * | 12/2004 | Uchigaki et al. | 600/584 |
| 6,866,675 B2 | * | 3/2005 | Perez et al. | 606/181 |
| 7,192,405 B2 | * | 3/2007 | DeNuzzio et al. | 600/583 |

(Continued)

FOREIGN PATENT DOCUMENTS

DE    103 25 699 B3    2/2005

(Continued)

OTHER PUBLICATIONS

EP 0 221 005 A2—Machine Translation, dated May 6, 1987.

(Continued)

*Primary Examiner* — Max Hindenburg
*Assistant Examiner* — Michael C Stout
(74) *Attorney, Agent, or Firm* — Woodard, Emhardt, Moriarty, McNett & Henry LLP (57) ABSTRACT

The invention concerns a process for producing a diagnostic test element for analyzing a body fluid in which a lancing member that can puncture a body part is provided with a collecting channel for body fluid obtained by the puncture, wherein the collecting channel exhibits capillary action, and wherein a sensor member for an optical or electrochemical measurement is connected to the lancing member. According to the invention, the sensor member and the lancing member can be joined together as interlocking connecting components wherein a measuring element of the sensor member is inserted into the collecting channel through an insertion opening of the lancing member.

44 Claims, 7 Drawing Sheets

U.S. PATENT DOCUMENTS

| | | | |
|---|---|---|---|
| 7,691,071 B2* | 4/2010 | Kojima et al. | 600/583 |
| 7,803,123 B2* | 9/2010 | Perez et al. | 600/583 |
| 2002/0052618 A1* | 5/2002 | Haar et al. | 606/181 |
| 2002/0103499 A1* | 8/2002 | Perez et al. | 606/182 |
| 2002/0177761 A1* | 11/2002 | Orloff et al. | 600/309 |
| 2003/0006332 A1* | 1/2003 | Appleby et al. | 242/362.2 |
| 2003/0028125 A1* | 2/2003 | Yuzhakov et al. | 600/583 |
| 2003/0083686 A1 | 5/2003 | Freeman | |
| 2003/0143113 A2* | 7/2003 | Yuzhakov et al. | 422/56 |
| 2004/0087873 A1* | 5/2004 | Erickson et al. | 600/573 |
| 2004/0186394 A1* | 9/2004 | Roe et al. | 600/583 |
| 2004/0225230 A1* | 11/2004 | Liamos et al. | 600/583 |
| 2005/0004494 A1* | 1/2005 | Perez et al. | 600/583 |
| 2005/0059166 A1 | 3/2005 | Markes | |
| 2005/0103624 A1* | 5/2005 | Bhullar et al. | 204/403.01 |
| 2005/0171567 A1* | 8/2005 | DeHart | 606/181 |
| 2006/0098203 A1* | 5/2006 | Kalveram | 356/446 |
| 2006/0200981 A1* | 9/2006 | Bhullar et al. | 29/847 |
| 2006/0229533 A1 | 10/2006 | Hoenes et al. | |
| 2007/0138026 A1* | 6/2007 | Fujiwara et al. | 205/777.5 |
| 2007/0224548 A1* | 9/2007 | Yang | 430/325 |
| 2007/0227907 A1* | 10/2007 | Shah et al. | 205/777.5 |

FOREIGN PATENT DOCUMENTS

| | | |
|---|---|---|
| EP | 0 073 558 A2 | 3/1983 |
| EP | 0 221 005 A2 | 5/1987 |
| EP | 1 413 249 A1 | 4/2004 |
| EP | 1 441 214 A2 | 7/2004 |
| EP | 1 491 143 A1 | 12/2004 |
| EP | 1 639 942 A1 | 3/2006 |
| WO | WO 97/42882 A1 | 11/1997 |
| WO | WO 2004/110275 A1 | 12/2004 |
| WO | WO 2005/104949 A1 | 11/2005 |

OTHER PUBLICATIONS

EP 1 491 143 A1—Machine Translation, dated Dec. 29, 2004.

International Application PCT/EP2006/009945 International Search Report mailed Feb. 2, 2007.

International Application PCT/US2007/065918 International Search Report mailed Aug. 23, 2007.

* cited by examiner

DIAGNOSTIC TEST ELEMENT AND PROCESS FOR ITS PRODUCTION

CROSS REFERENCE TO RELATED APPLICATIONS

This application is a continuation of International Application No. PCT/US2007/065918, filed Apr. 4, 2007, which claims the benefit of International Application PCT/EP2006/009945, filed Oct. 15, 2006, which claims the benefit of European Application 05022535.8 filed Oct. 15, 2005, the entire disclosures of which are hereby incorporated by reference.

TECHNICAL FIELD

The invention generally concerns a process for producing a diagnostic test element suitable for analyzing a body fluid. The diagnostic test element has a lancing member that can puncture a body part to obtain a body fluid sample. The lancing member is provided with a capillary collecting channel for body fluid obtained by the puncture. The test element also has a sensor member for an optical or electrochemical measurement is connected to the lancing member.

BACKGROUND

Blood sugar self-monitoring is usually carried out several times daily as part of an insulin treatment regimen to control diabetes. It is therefore desirable to minimize the number of handling steps the patient is required to carry out and to ensure a relatively painless and highly reliable blood sugar measurement. Disposable measurement articles are used for hygienic reasons. In conventional blood sugar measurements, samples are generated by finger pricking with lancets and the measurement is carried out on separate detection elements. This requires a large number of handling steps by the patient which can result in errors. Further disadvantages are blood volumes that are too large, non-robust sample transfer procedures, and lack of integration that requires the patient to organize and handle separate devices and disposable supplies.

SUMMARY

Taking this as a starting point, the object of the invention is to further improve the test elements and processes for their production known in the prior art, and in particular to enable practicable mass production and use of more highly integrated test elements that are cost-effective and at the same time reliable, while also allowing relatively simple instrument technology.

The combination of features stated in the independent claims is proposed to achieve this object. Advantageous embodiments and further developments of the invention are derived from the dependent claims.

The idea behind the invention is to use test elements in which a small volume sample can be collected and reliably analyzed. A production process is proposed for such test elements in which a lancing member that can puncture a body part is provided with a collecting channel, preferably exhibiting capillary action, for the body fluid obtained by the puncture, and a sensor member for an optical or electrochemical measurement is connected to the lancing member. According to the invention the sensor member and the lancing member are joined together as interlocking connecting components, such that a measuring element of the sensor member is inserted into the collecting channel through an insertion opening in the lancing member. This permits the parts to be separately produced in optimized manufacturing steps at low production costs and subsequently integrated into a compact configuration by a simple interlocking connection. In this configuration a small amount of sample in the collecting channel is sufficient to reliably contact and wet the sensor located therein. This also allows precise positioning tolerances in the test element production process, thereby simplifying tolerance management on the instrument side. In particular, it is not necessary to actively transfer the sample to a separate sensor that is not in the direct sample flow, thereby making possible reliable measurements, even with very small samples of 100 nanoliters or less. Reliable measurement is of special importance because automation of handling steps by the system reduces the demand of ability of the patient to monitor and control the process.

The invention is described in more detail in the following with reference to the embodiment examples shown schematically in the drawing.

DETAILED DESCRIPTION

The test elements 10 shown in the drawing can be used as consumables for blood sugar measurement in a hand-held device 12 designed for this purpose wherein glucose can be detected directly in the test element using a minimal amount of sample. For this purpose the test elements 10 comprise a lancing member 14 having a slot-shaped collecting channel 16, a sensor member 18 for an optical or electrochemical measurement in the collecting channel 16, and a holder 20 for the lancing member and the sensor member.

Figure 1:
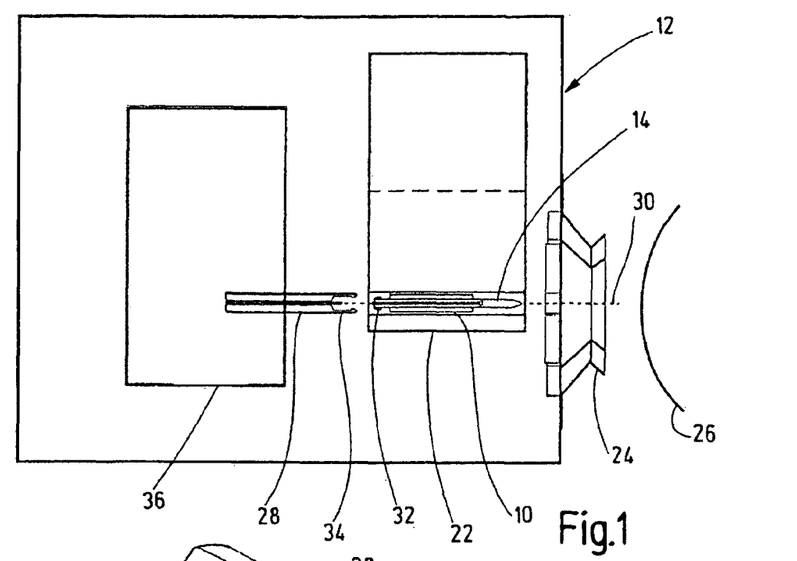
FIG. 1 shows a blood sugar measuring instrument with a diagnostic test element used therein as a consumable unit in a diagrammatic representation.

As illustrated in FIG. 1 a plurality of test elements 10 in, for example, a drum-like magazine 22 can be moved successively into an active working position with respect to a ring-shaped support 24 with a puncture opening for a finger tip 26 of a user. A lancing drive 28 which engages into the magazine 22 enables a reciprocating lancing movement of the test element 10 along a lancing axis 30. In this connection the tip of the lancing member 14 points in the distal direction towards the body part while a coupling end 32 of the test element is coupled to a suitable gripper member 34 of the lancing drive 28 for mechanical drive and signal coupling. The body fluid (blood or tissue fluid) which is taken up in the collecting channel 16 by the lancing process, can be directly optically or electrochemically analyzed by the sensor member 18. The signal analysis takes place in an evaluation unit 36 in the instrument. This also enables the result of the measurement to be displayed to the user so that the blood sugar can be checked on the spot without complicated handling steps.

Figures 2, 3:
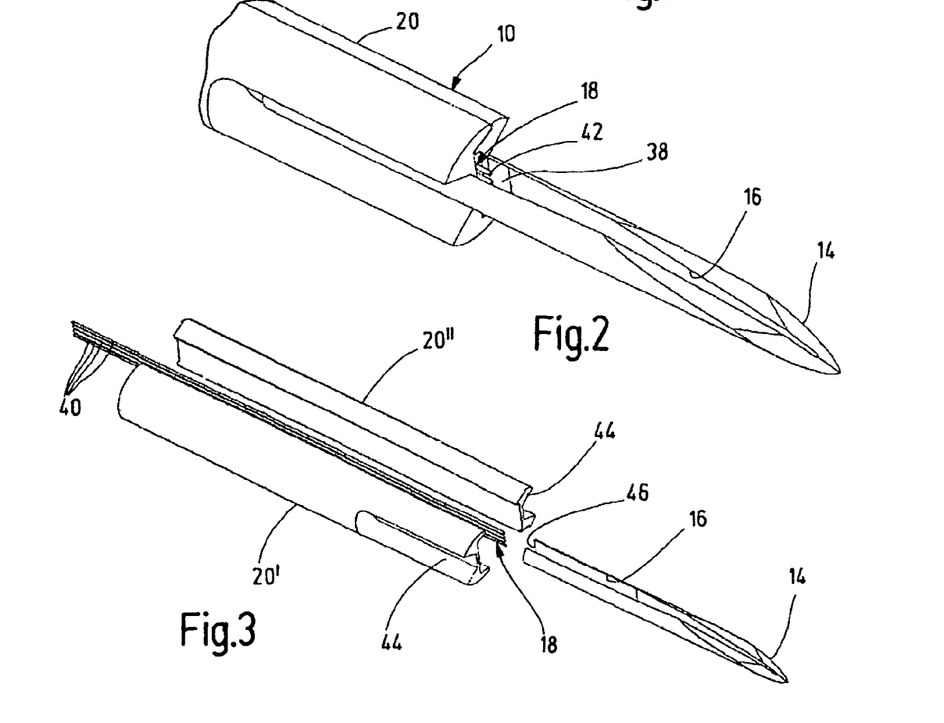
FIG. 2 shows an embodiment of the test element in a partial perspective representation.
FIG. 3 shows an exploded diagram of the test element according to FIG. 2 comprising a lancing member, a sensor based on wire electrodes and a holder.

As shown in FIGS. 2 and 3 the shaft-like elongate lancing member 14 has a transverse continuous longitudinal slot forming the collecting channel 16. This enables, optionally by means of capillary action, the transfer of a microscopic amount of liquid into the proximal measuring zone 38. The elongate slit opening on both sides ensures an effective liquid uptake without the risk of blockage by cell components. In order to collect blood as gently and pain-free as possible, the collecting channel 16 is designed to have a volume of only a few tens of nanoliters.

According to FIG. 3 the sensor member 18 has several parallel electrode wires 40 in order to achieve a high degree of measurement reliability through redundant detection of measured values. The electrode wires are either continuously coated with a test reagent, or only coated at the ends in order to enable electrochemical detection of the analyte in the body fluid. For this purpose the coated ends of the wire protrude in a self-supporting manner into the internal cross-section of the collecting channel 16 in the area of the measuring zone 38. In this manner the wire ends form a measuring element 42 which is electrically insulated inside the channel from the channel wall by a free space, and body fluid can flow against and wet the front of the measuring element. In this arrangement a few nanoliters of blood are sufficient for an integrated detection of measured values in the test element 10.

Some specific methods for manufacturing test elements 10 configured in this manner are described in the following. In general the sensor member 18 and the lancing member 14 are joined in an interlocking manner whereby the measuring element 42 is inserted into the collecting channel 16.

In the embodiment according to FIGS. 2 and 3 the electrode wires 40 are clamped between two halves 20', 20" of the longitudinally divided holder 20 whereby grooves that are not shown ensure well-defined positioning of the wires. Then the fork-shaped end of the lancing member 14 which is prefabricated from a metallic wire material by a combination of grinding and laser cutting processes or etching is mounted axially on the receiving grooves 44 of the holder 20. In this process the measuring element 42 of the sensor member 18 is inserted via the proximal slot opening 46 into the collecting channel 16 and moved into the specified position.

Figures 4, 5:
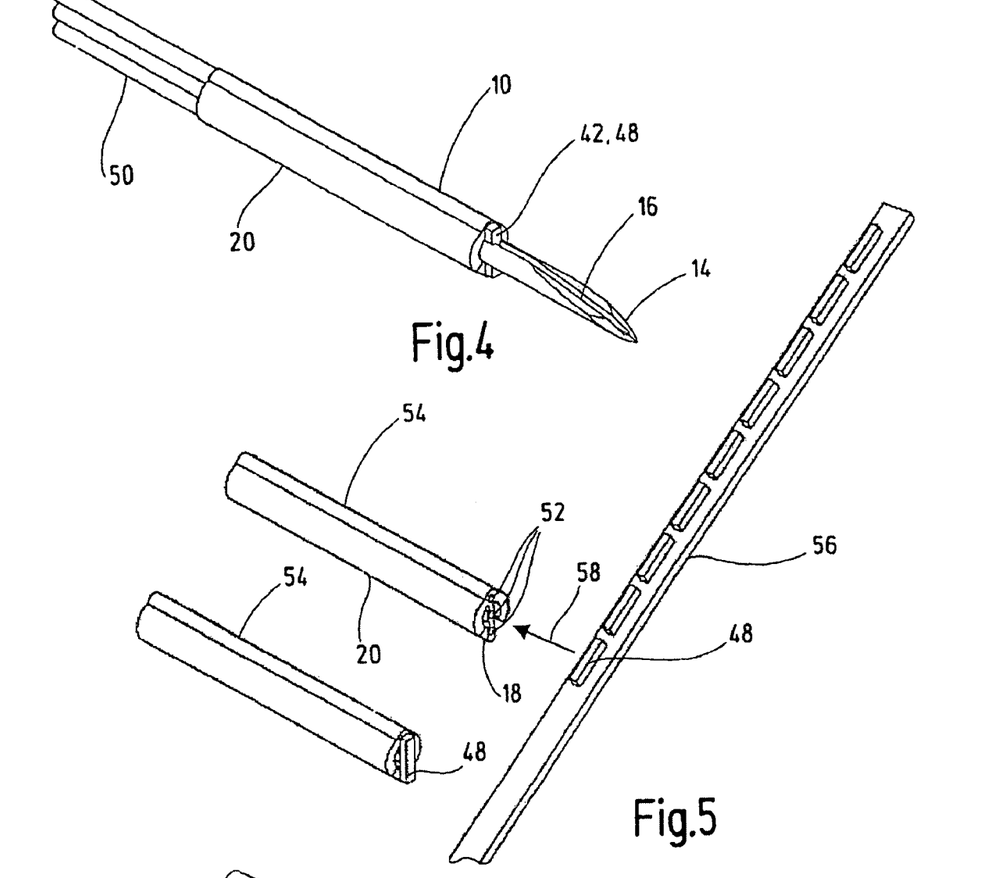
FIG. 4 shows an embodiment of an optical test element in a perspective view.
FIGS. 5 and 6 show various production steps for the test element according to FIG. 4.

FIG. 4 shows another variant of a test element 10 which is equipped with optical light guides and a reagent pad 48 as a measuring element 42 for a reflection-photometric measurement. The signal is coupled out by an end-face contact with light guides 50 on the instrument side which have a suitable diameter for a reliable signal transmission.

As shown in FIG. 5 a composite element 54 consisting of three parallel light guides 52 and a plastic holder 20 is manufactured by coextrusion and then subsequent division into sections. The distal front end of the composite part 54 prefabricated in this manner is then provided with a reagent pad 48 which is dispensed from a tape 56 like a self-adhesive label and glued onto the free ends of the light guides (arrow 58).

Figure 6:
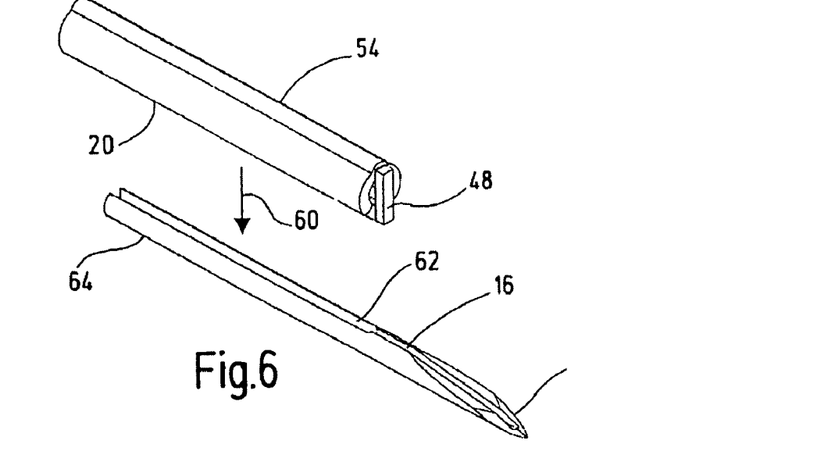

In another manufacturing step illustrated in FIG. 6 the composite part 54 is subsequently clipped or latched onto the lancing member 14 in the direction of the arrow 60. In this process the reagent pad 48 is also inserted transversely into the collecting channel 16 via the longitudinal slit opening 62 to obtain the configuration shown in FIG. 4. The holder 20 embraces the shaft 64 of the lancing member 14 which is slotted and elongated on the rear side, in a shell-shaped manner. This facilitates low-cost production because holder 20 can be combined with the lancing member 14 by a fast snap-on process. When used for measurement the central fiber of the three fibers comprising light guide 52 enables irradiation of the measuring light which is reflected from the rear side of the reagent pad 48 and is detected via the two outer fibers of light guide 52 for a duplicate photometric measurement.

It is also conceivable that the light guides or the reagent pad 48 are provided with a fluorescent indicator as described in the patent application WO 03/097859 and to which explicit reference is herewith made. Specifically, a liquid polymerizable composition comprising a detection reagent can be applied. After application of the sample to the front side of such a sensor, exciting light, e.g. UV light, is beamed in through a light guide. The fluorescence, e.g. bluelight, generated through the reaction of the analyte with the detection reagent in the polymer layer is detected via the light guide with a detector. Preferably, the polymer layer has a thickness of about 50 microns or less, which allows for comparably short reaction times for generating the fluorescence light when the analyte is detected. In this way, the reaction or measurement time can be shorter than 2 s, preferably shorter than 1 s, thereby enabling a measurement while the lancing member is still in the skin of the body part. It has been found that leaving the lancing member inserted for such a short time interval is fully acceptable for most users.

Figure 7:
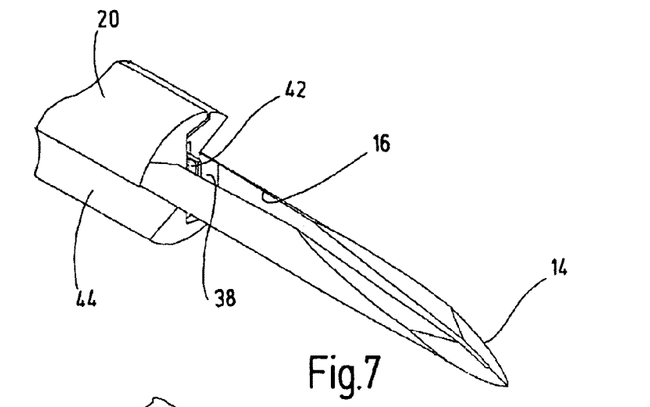
FIGS. 7 and 8 show another embodiment of an electrochemical test element in a representation corresponding to FIGS. 2 and 3.
Figures 8, 9:
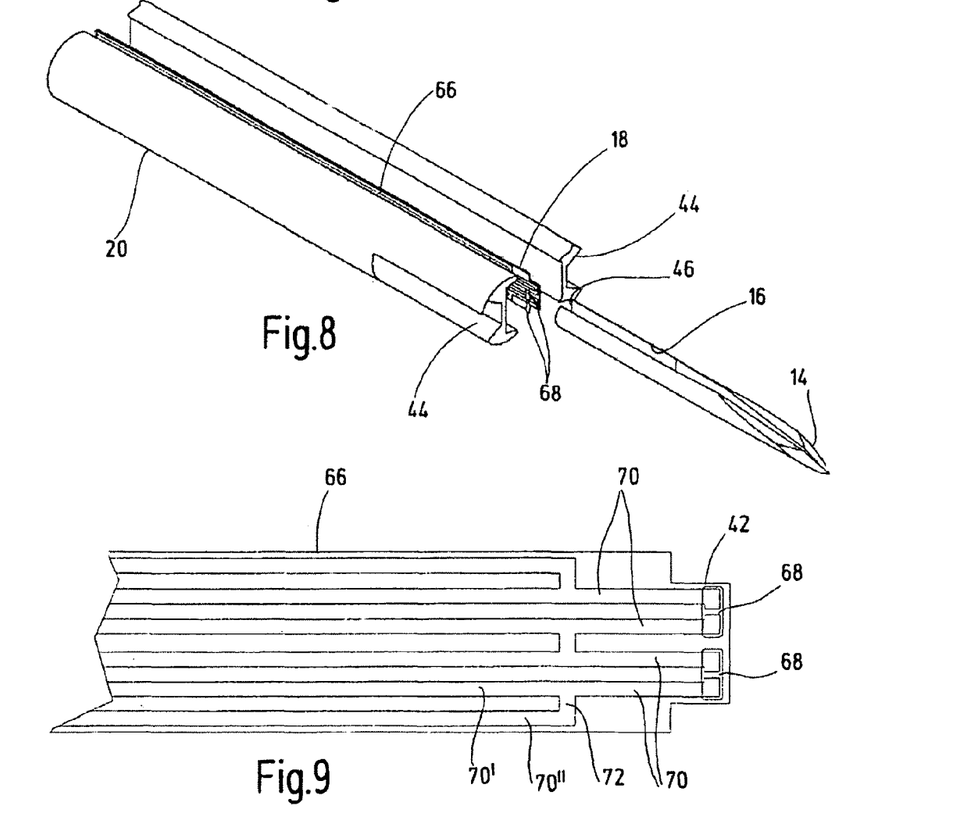
FIG. 9 shows the sensor member of the test element according to FIG. 7 in a partial side-view.

The embodiment shown in FIGS. 7 to 9 differs from the example of FIGS. 2 and 3 essentially in that instead of coated electrode wires, a printed circuit board 66 is used as a prefabricated sensor member 18. The distal end of the printed circuit board 66 is provided with two electrically connected reagent fields 68 which protrude freely into the measuring zone 38 to form a measuring element 42. Also in this case it is manufactured by first clamping the printed circuit board 66 into the two-part holder 20 and then axially mounting the lancing member 14 so that the fork-shaped ends of the lancing member 14 engage in the grooves 44 and the measuring element 42 is positioned in the channel cross-section.

FIG. 9 shows the electrical connection of the reagent fields 68 via in this case two conductor paths 70 on the printed circuit board 66. Each of the conductor paths 70 branch over one conductor bridge 72 into a primary conductor path 70' and a secondary conductor path 70" in order to thus be able to carry out an electrical continuity test at least up to the conductor bridge 72 and to detect any interruptions of the conductor paths. This, in addition to the redundant double measurement, further increases the functional reliability.

Figure 10:
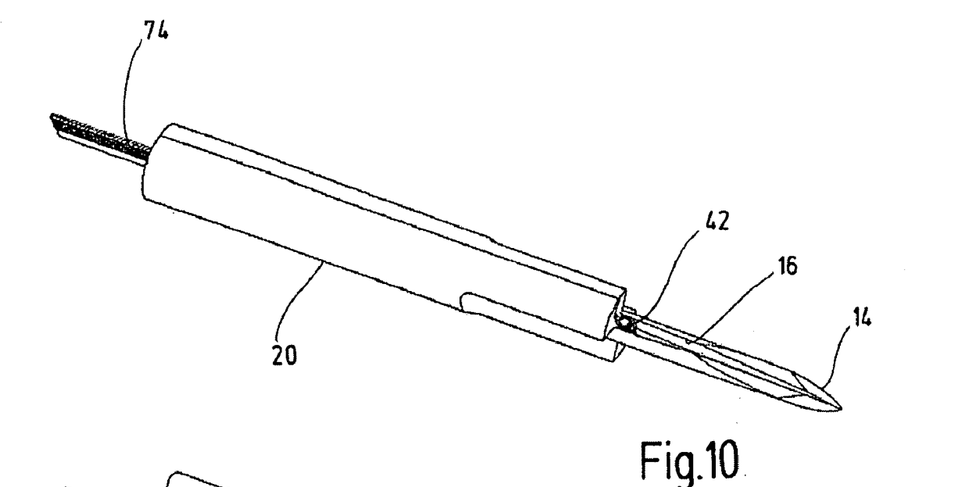
FIGS. 10 to 12 show another embodiment of an electrochemical test element in a representation corresponding to FIGS. 7 to 9.
Figure 11:
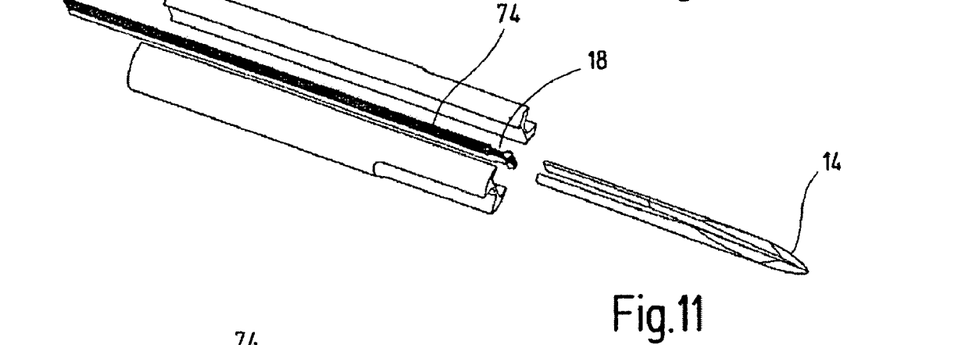
Figure 12:
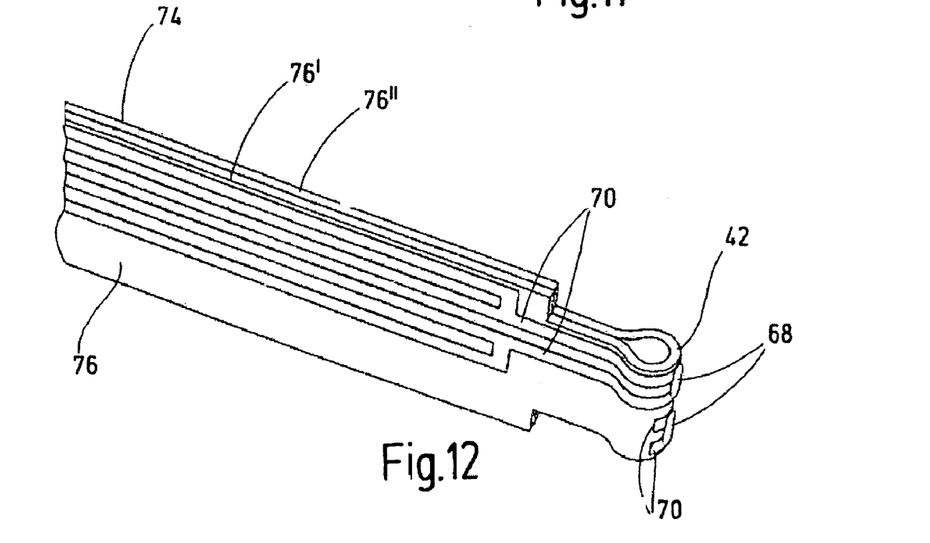

A similar embodiment to FIGS. 7 to 9 is shown in FIGS. 10 to 12. However, instead of the printed circuit board 66, a test strip 74 which is folded transversely is provided as a sensor element 18. It is again assembled as described above by clamping the test strip 74 into the holder 20 and axially mounting the lancing member 14.

As also illustrated in FIG. 12, the concept of the folded test strip 74 has various advantages. The manufacture can start with a planar structure in the form of a thin flexible foil strip. This is provided with conductor paths 70 and with reagent fields 68 at their contact ends while still in an unfolded form. Subsequently the equipped foil strips are folded up in the middle so that the strip halves 76', 76" can be glued together. The reagent fields 68 then protrude freely from the front face in the area of the rounded bending site so that liquid can flow against and wet the reagent fields in the channel 16.

Special process steps are illustrated in FIGS. 13 to 21 which allow an advantageous continuous mass production through different stations.

Figure 13:
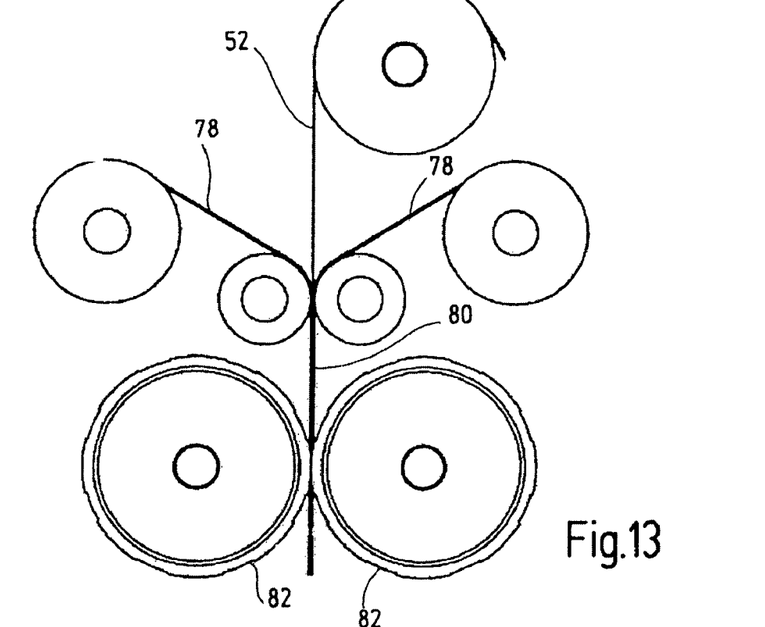
FIG. 13 shows a device for the continuous manufacture of a light guide composite member of the test element.
Figure 14:
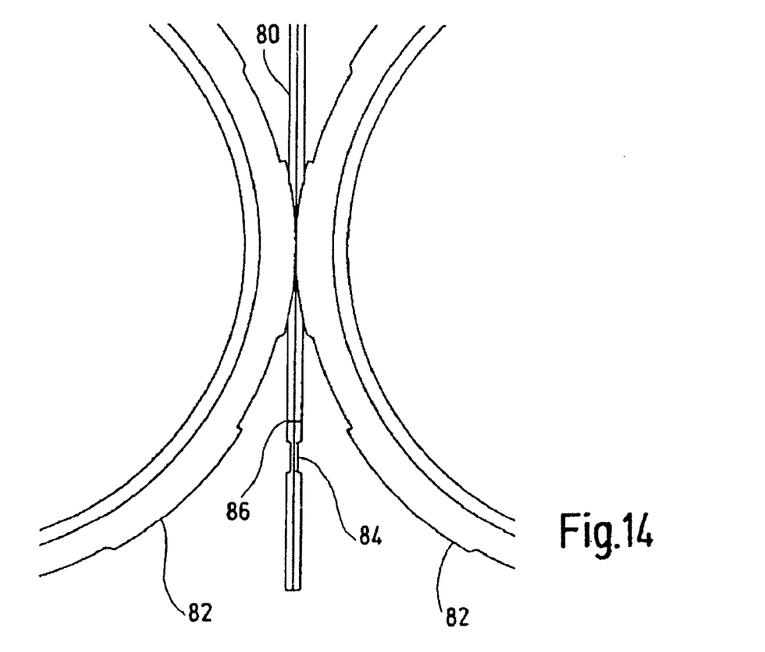
FIG. 14 shows an enlarged section of FIG. 13.

Firstly according to FIG. 13 three parallel light guides 52 in the form of polymer fibers are fed from reels and laminated between the foil strips 78 to form a composite strand 80. In a subsequent embossing station the outer contour of the composite strand 80 is shaped by embossing rollers 82. As shown in FIG. 14 this enables both the receiving grooves 44 and a coupling structure 84 for a positive locking gripper coupling to be created. The reshaped composite strand 80 is subsequently severed at the cutting lines 86 to thus obtain the composite parts 54 shown in FIG. 15.

Figures 15, 16:
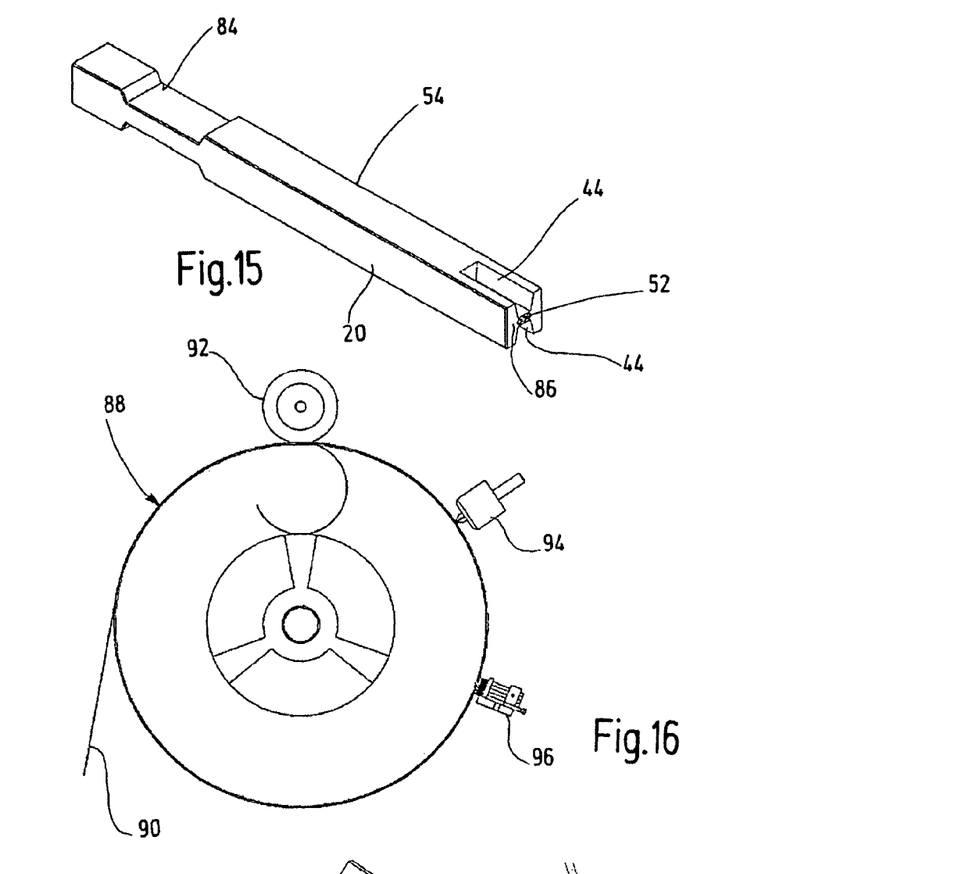
FIG. 15 shows the light guide composite member in a perspective view.
FIG. 16 shows a device for producing label-like measuring elements for the test element in a side-view.
Figure 17:
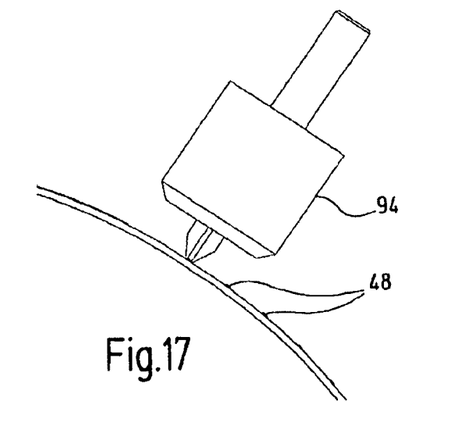
FIGS. 17 and 18 show enlarged sections of FIG. 16.
Figure 18:
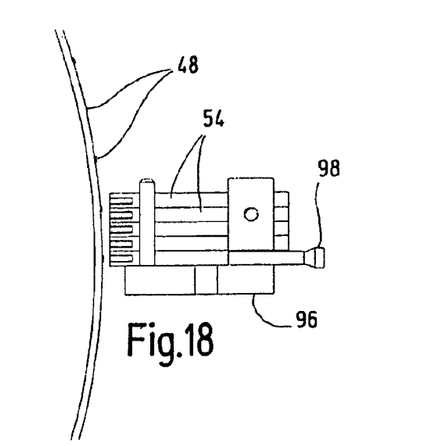

The distal front end 86 of the composite part 54 is equipped with measuring elements in the rotary station 88 shown in FIG. 16. The reagent pads 84 provided for this should have an adequate homogeneity in the required small dimensions—for example 200×400 μm. For this purpose a test chemistry is firstly knife-coated over a large area of a wide test tape 90. Then the test tape 90 is reduced to a narrow central strip by parallel cutting rollers 92. As shown in FIG. 17, the desired reagent pads 48 can be cut out of the central strip by a punching device 94. The reagent pads 48 are finally applied to the composite parts 54 at another rotary position of the rotary station 88. For this purpose a transfer device 96 is provided in which a plurality of composite parts 54 are stacked. The transfer takes place by means of a pneumatic unit 98 which successively brings the composite parts 54 into an end face contact with the self-adhesive reagent pads 48 by means of a blast of air.

Figure 19:
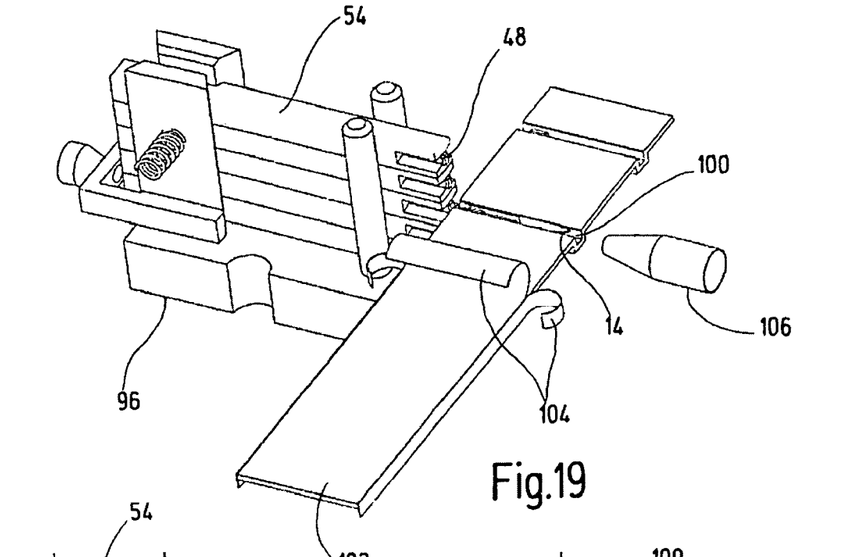
FIG. 19 shows a device for equipping test elements with lancing members in a diagrammatic representation.
Figures 20, 21:
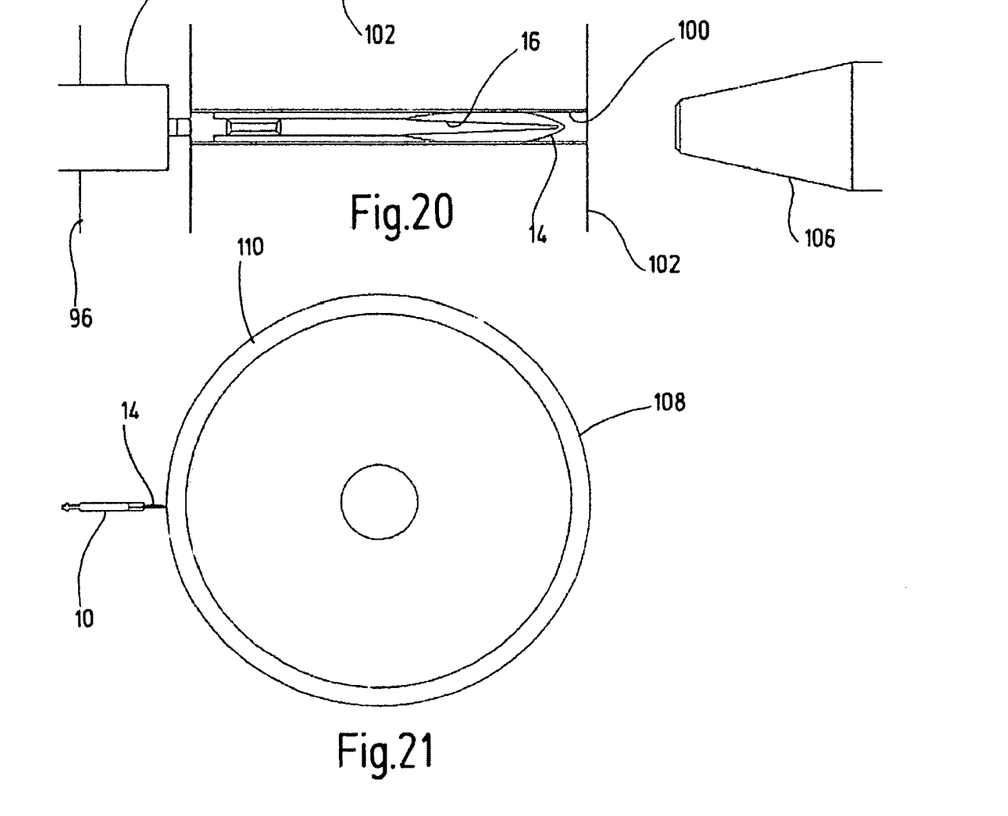
FIG. 20 shows a sectional top-view of the device according to FIG. 19.
FIG. 21 shows a device for hydrophilically coating the lancing members of the test elements.

The composite parts 54 prepared in this manner are provided with lancing members 14 in the assembly station shown in FIGS. 19 and 20. The prefabricated lancing members 14 can in this process be conveyed to the transfer device 96 in depressions 100 of a blister tape 102. The test element storage in the depressions 100 in a blister tape 102 sealed by cover foils 104 also enables a separate sterilization of the lancing members 14, for example by irradiation, without damaging the test chemistry. The axial sliding assembly motion of the lancing members 14 onto the composite parts 54 is in turn effected by means of a blast of air by a pneumatic unit 106.

The metallic lancing members 14 can be provided with a hydrophilic layer in order to support the uptake of body fluid in the collecting channel 16. For this purpose the lancing members 14, either before or after they are mounted on the finally packaged test elements 10, can be brought into contact with an absorbent application ring 110 at the application station 108 shown in FIG. 21, the ring being impregnated with a suitable hydrophilic coating substance. The amount of substance applied to the lancing member 14 can then be accurately controlled by means of the contact time.

A further possibility to produce the light fiber structure is to generate the fibers in situ on or within an embossed part of a tape or foil-like carrier. In this process a thin layer of low refractive index transparent polymer, for example epoxy, is deposited onto a structural substrate to form a base layer. This is then over-coated by a thin layer of photosensitive high refractive index transparent polymer. This layer is processed by UV photolithography to selectively remove material, leaving the light guides as generally parallel strips of high refractive index polymer bonded to the low refractive index base layer. Finally, a layer of low refractive index polymer is flow-coated over the light guides and polymerized to form a solid layer. The result is that high refractive index light guides are surrounded on all sides by lower refractive index transparent polymer, forming functional independent light guides. Suitable materials are available commercially, for example, under the tradenames EpoCore and EpoClad epoxy polymer resins supplied by the German company Micro Resist Technology. Particular advantages of such photolithographic processes for manufacturing the parallel light guides include low cost volume production and the ability to vary the geometry of the light guides along their length. For example, the light guides may be tapered to transition from a small reagent pad to a larger optical interface with the measuring instrument.

What is claimed is:

1. Process for producing a diagnostic test element for analyzing a body fluid in which a lancing member that can puncture a body part is provided with a capillary collecting channel for body fluid obtained by the puncture and a sensor member for an optical or electrochemical measurement is connected to the lancing member, wherein the sensor member and the lancing member can be joined together as interlocking connecting components wherein a measuring element of the sensor member is inserted into the collecting channel through an insertion opening of the lancing member, wherein the collecting channel is formed as a transverse continuous slot in the lancing member, said slot being open at a proximal aperture, wherein the sensor member is inserted into the slot through the proximal aperture for directly depositing the body fluid from the capillary channel directly onto the measuring element of the sensor member, wherein a holder positions the measuring element in the capillary collecting channel, wherein the capillary collecting channel establishes a path for directly depositing the body fluid on the sensor member, wherein the lancing member slot holds the diagnostic test element together.

2. Process according to claim 1, wherein the sensor member and the lancing member can be joined together along a connecting axis running in a longitudinal direction of the collecting channel.

3. Process according to claim 1, wherein the sensor member is inserted transversely into the collecting channel which has an open longitudinal side.

4. Process according to claim 1, wherein the collecting channel has a channel wall, wherein the measuring element in an interior of the collecting channel is arranged such that the measuring element is electrically isolated from the channel wall.

5. Process according to claim 1, wherein the measuring element protrudes in a self-supporting manner into an internal cross-section of the collecting channel.

6. Process according to claim 1, wherein the measuring element is arranged as a flow obstacle onto which the body fluid can flow in a proximal flow cross-section of the collecting channel.

7. Process according to claim 1, wherein the sensor member is connected to the lancing member by a clip, snap or latched connection.

8. Process according to claim 1, wherein the lancing member and the sensor member are connected together by a plug connection in which a proximal section of the lancing member is plugged into a receiving opening of the sensor member.

9. Process according to claim 1, wherein the sensor member is provided with a light guide in order to optically couple the sensor member to the measuring element.

10. Process according to claim 1, wherein a plurality of light guides are integrated into corresponding sections of a embossed support tape or substrate, and that each section of tape or substrate is connected to a lancing element.

11. Process according to claim 10, wherein the light guides are built during the integration step in situ by a photolithographic process.

12. Process according to claim 10, wherein the light guides have a variable cross-section over a length of the light guides.

13. Process according to claim 9, wherein the light guide that is fed from a reel and comprises a polymer fibre, is continuously combined with foil strips to form a composite.

14. Process according to claim 9, wherein the light guide is combined with a surrounding holding structure to form a composite part by means of a co-extrusion process.

15. Process according to claim 14, wherein an outer contour of the composite part is formed by embossing or embossing-cutting processes in order to receive the lancing element at a distal end of the continuous light guide composite and to enable a drive coupling and/or signal coupling at a proximal end of the continuous light guide composite.

16. Process according to claim 15, wherein individual structural units are cut to length from the composite part by laser cutting or mechanical cutting means.

17. Process according to claim 1, wherein the measuring element is provided as a section of reagent tape by dividing a reagent tape provided with test chemistry into pieces.

18. Process according to claim 1, wherein the measuring element is applied to an end face of the sensor member pointing towards the collecting channel in the connected state.

19. Process according to claim 1, wherein the measuring element is applied to the sensor member by a label application method in which the measuring element provided on a front side with a test reagent and on a rear side with an adhesive layer is prepared in the form of a self-adhesive label by dividing a tape into pieces.

20. Process according to claim 1, wherein the measuring element is formed by an end section of at least one electrode wire that is continuously coated with a test reagent.

21. Process according to claim 1, wherein the sensor member is formed by an electrochemical test strip, said test strip being provided with electrical conductor paths and at least one reagent field contacted by the conductor paths as a measuring element.

22. Process according to claim 21, wherein the test strip provided with longitudinal conductor paths is folded centrally and transversely whereby at least one measuring element is contacted with the conductor paths at the bending site.

23. Process according to claim 21, wherein primary conductor paths for an analyte detection and secondary conductor paths for an electrical continuity test of the primary conductor paths are applied to the test strip.

24. Process according to claim 1, wherein the measuring element includes at least two measuring elements that are in particular designed as reagent fields, are arranged in a measuring zone of the sensor member for a redundant duplicate measurement.

25. Process according to claim 1, wherein the measuring element is attached to the holder such that the measuring element overhangs distally and extends into the collecting channel, wherein the measuring element overhands more than 50 μm.

26. Process according to claim 1, wherein a guide means for inserting the lancing member is incorporated into the holder and is in particular in the form of a groove.

27. Process according to claim 1, wherein at least two parts of the holder are connected together while enclosing optical or electrical signal conductors, the holder parts being provided with recesses for the defined positioning of the signal conductors.

28. Process according to claim 1, wherein the lancing member is formed as a round or flat lancet by a cutting process and in particular by laser cutting or by an etching process.

29. Process according claim 1, wherein a hydrophilic layer is applied to the lancing member.

30. Process according to claim 1, wherein the lancing member is provided with a hydrophilic layer before being connected to the sensor member in an immersion bath or subsequently thereto preferably by spraying.

31. Process according to claim 1, wherein a plurality of test elements manufactured in a continuous process are packaged in a sterile manner as single-use articles in a magazine.

32. A process, comprising:
providing a lancing member with a slot-shaped collecting channel and a forked-shaped proximal end, wherein the collecting channel is a slot that extends longitudinally along the lancing member from the forked-shaped proximal end to a distal end, wherein the fork-shaped proximal end has a proximal slit opening that opens on opposing sides of the lancing member, wherein the collecting channel is hydrophilic to draw fluid via capillary action, wherein the proximal slit of the forked shaped end and the collecting channel are formed in a unitary piece in which the proximal slit extends completely through the unitary piece and the collecting channel extends only partially through the unitary piece that forms the lancing member;
securing a measuring element to a holder that includes receiving grooves to form a sensor member; and
joining the sensor member to the lancing member in an interlocking fashion by mounting the forked-shaped proximal end of the lancing member into receiving grooves of the holder such that the sensor member is inserted into the slot-shaped collecting channel via the proximal slit opening at the forked-shaped proximal end of the lancing member, wherein the fork shaped end of the lancing member holds the sensor member and the lancing member together, and the collecting channel is aligned to deposit the fluid onto the sensor member via the fork shaped end.

33. The process of claim 32, wherein said providing the lancing member includes forming forked-shaped proximal end via a laser cutting process.

34. The process of claim 32, further comprising:
wherein the sensor member has a reagent to analyze body fluid; and
wherein said joining the sensor member to the lancing member includes inserting the reagent inside the slot-shaped collecting channel.

35. The process of claim 32, wherein said joining the sensor member to the lancing member includes inserting the sensor member into the slot-shaped collecting channel in an axial direction relative to the lancing member.

36. A process, comprising:
providing a lancing member with a slot-shaped collecting channel and a forked-shaped proximal end, wherein the collecting channel is a slot that extends longitudinally along the lancing member from the forked-shaped proximal end to a distal end, wherein the fork-shaped proximal end has a proximal slit opening that opens on opposing sides of the lancing member, wherein the lancing member is made from a section of metallic wire, wherein the forked-shaped proximal end and the slot-shaped collecting channel are fabricated in the section of metallic wire;

providing a sensor member configured to analyze body fluid, wherein the sensor member and the lancing member are separate components; and joining a sensor member directly to the lancing member through an interlocking connection by inserting the sensor member into the slot-shaped collecting channel via the proximal slit opening at the forked-shaped proximal end of the lancing member, wherein during said joining the forked-shaped proximal end holds together the sensor member and the lancing member, wherein the interlocking connection establishes a path for the body fluid to be deposited directly onto the sensor member from the slot-shaped collecting channel via capillary action.

37. The process of claim 36, further comprising:
wherein the sensor member has a reagent to analyze body fluid; and
wherein said joining the sensor member to the lancing member includes inserting the reagent inside the slot-shaped collecting channel.

38. The process of claim 36, further comprising:
securing the sensor to a holder that includes receiving grooves; and
mounting the forked-shaped proximal end of the lancing member into receiving grooves of the holder by inserting the sensor member into the slot-shaped collecting channel in an axial direction relative to the lancing member.

39. The process of claim 36, further comprising:
forming a composite element with the sensor member and a holder;
attaching a reagent pad to the sensor member; and
wherein said joining the sensor member to the lancing member includes latching the reagent pad into the slot-shaped collecting channel via the proximal slit opening in a direction that is transverse to the lancing member.

40. The process of claim 36, further comprising:
clamping the sensor member between two halves of a holder; and
wherein the two halves of the holder clamped around the sensor member are inserted in the forked-shaped proximal end of the lancing member during said joining.

41. Process according to claim 1, further comprising:
clamping the sensor member between two halves of a holder; and
wherein the lancing member at the slot at least in part holds the two halves of the holder clamped around the sensor member.

42. The process of claim 32, further comprising:
clamping the sensor member between two halves of a holder; and
wherein the forked-shaped end at least in part holds the two halves of the holder clamped around the sensor member.

43. The process of claim 32, further comprising:
prefabricating the forked shaped end and the collecting channel from a metallic wire, wherein the unitary piece is a portion of the metallic wire.

44. The process of claim 32, further comprising:
treating the collecting channel to be hydrophilic.

* * * * *